US007956214B2

(12) United States Patent
Chidambaram et al.

(10) Patent No.: US 7,956,214 B2
(45) Date of Patent: Jun. 7, 2011

(54) PROCESS FOR THE PREPARATION OF ANILINE-DERIVED THYROID RECEPTOR LIGANDS

(75) Inventors: Ramakrishnan Chidambaram, Pennington, NJ (US); Joydeep Kant, Cherry Hill, NJ (US); Raymond E. Weaver, Hampton, NJ (US); Jurong Yu, Dayton, NJ (US); Arun Ghosh, Madison, CT (US)

(73) Assignees: Karo Bio AB, Huddinge (SE); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/456,313

(22) Filed: Jun. 15, 2009

(65) Prior Publication Data

US 2009/0326263 A1 Dec. 31, 2009

Related U.S. Application Data

(62) Division of application No. 10/936,062, filed on Sep. 8, 2004, now abandoned, which is a division of application No. 10/273,268, filed on Oct. 17, 2002, now Pat. No. 6,806,381.

(60) Provisional application No. 60/336,318, filed on Nov. 2, 2001.

(51) Int. Cl.
*C07C 309/00* (2006.01)
(52) U.S. Cl. ....................................................... 562/30
(58) Field of Classification Search ........................ None
See application file for complete search history.

(56) References Cited

U.S. PATENT DOCUMENTS

| 2,596,393 | A | 5/1952 | Fitz Gerald |
| 3,544,623 | A | 12/1970 | Hansen et al. |
| 3,674,836 | A | 7/1972 | Creger |
| 3,879,557 | A | 4/1975 | Kaiser et al. |
| 3,983,140 | A | 9/1976 | Endo et al. |
| 4,027,009 | A | 5/1977 | Grier et al. |
| 4,231,938 | A | 11/1980 | Monaghan et al. |
| 4,346,227 | A | 8/1982 | Terahara et al. |
| 4,379,785 | A | 4/1983 | Weyer et al. |
| 4,448,784 | A | 5/1984 | Glamkowski et al. |
| 4,450,171 | A | 5/1984 | Hoffman et al. |
| 4,499,289 | A | 2/1985 | Baran et al. |
| 4,572,912 | A | 2/1986 | Yoshioka et al. |
| 4,613,610 | A | 9/1986 | Wareing |
| 4,639,436 | A | 1/1987 | Junge et al. |
| 4,647,576 | A | 3/1987 | Hoefle et al. |
| 4,681,893 | A | 7/1987 | Roth |
| 4,686,237 | A | 8/1987 | Anderson |

(Continued)

FOREIGN PATENT DOCUMENTS

EP 0 142 146 5/1985

(Continued)

OTHER PUBLICATIONS

Gilman et al., Journal of the American Chemical Society (1935), 57, 909-12.*

(Continued)

*Primary Examiner* — Karl J Puttlitz
(74) *Attorney, Agent, or Firm* — Todd E. Garabedian; Wiggin and Dana LLP (57) ABSTRACT

Provided are processes for the synthesis of aniline derivatives, specifically certain aniline derivatives which have activity as thyroid receptor ligands.

2 Claims, 1 Drawing Sheet

U.S. PATENT DOCUMENTS

| | | | |
|---|---|---|---|
| 4,759,923 A | 7/1988 | Buntin et al. | |
| 4,871,721 A | 10/1989 | Biller | |
| 4,904,769 A | 2/1990 | Rauenbusch | |
| 4,924,024 A | 5/1990 | Biller | |
| 5,006,530 A | 4/1991 | Angerbauer et al. | |
| 5,177,080 A | 1/1993 | Angerbauer et al. | |
| 5,273,995 A | 12/1993 | Roth | |
| 5,346,701 A | 9/1994 | Heiber et al. | |
| 5,354,772 A | 10/1994 | Kathawala | |
| 5,385,929 A | 1/1995 | Bjorge et al. | |
| 5,401,772 A | 3/1995 | Yokoyama et al. | 514/539 |
| 5,569,674 A | 10/1996 | Yokoyama et al. | 514/539 |
| 5,594,016 A | 1/1997 | Ueno et al. | |
| 5,595,872 A | 1/1997 | Wetterau, II et al. | |
| 5,614,492 A | 3/1997 | Habener | |
| 5,631,224 A | 5/1997 | Efendic et al. | |
| 5,654,468 A | 8/1997 | Yokoyama et al. | 560/43 |
| 5,686,104 A | 11/1997 | Mills et al. | |
| 5,712,279 A | 1/1998 | Biller et al. | |
| 5,712,396 A | 1/1998 | Magnin et al. | |
| 5,739,135 A | 4/1998 | Biller et al. | |
| 5,760,246 A | 6/1998 | Biller et al. | |
| 5,827,875 A | 10/1998 | Dickson, Jr. et al. | |
| 5,885,983 A | 3/1999 | Biller et al. | |
| 5,962,440 A | 10/1999 | Sulsky | |
| 6,194,454 B1 | 2/2001 | Dow | 514/522 |
| 6,414,126 B1 | 7/2002 | Ellsworth et al. | |
| 6,548,529 B1 | 4/2003 | Robl et al. | |
| 2001/0051657 A1 | 12/2001 | Chiang et al. | |

FOREIGN PATENT DOCUMENTS

| | | |
|---|---|---|
| EP | 0 221 025 | 5/1987 |
| GB | 2 205 837 | 12/1988 |
| JP | 03-291241 | 12/1991 |
| WO | WO 86/03488 | 6/1986 |
| WO | WO 86/07054 | 12/1986 |
| WO | WO 01/60784 A1 | 8/2001 |
| WO | WO 01/72692 A1 | 10/2001 |

OTHER PUBLICATIONS

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, pp. 1-40 (1996).

Blank, B. et al., "Thyromimetics. I. The Synthesis and Hypocholesteremic Activity of Some 3' and 3',5'-Alkyl and Aryl-3,5-diiodothyronines", J. Med. Chem., vol. 6, pp. 554-560 (1963).

Bowman, D.F. et al., "Oxidation of Alkoxyphenols. Part VIII. Further Examples of Trimerisation to Spiroketals", J. Chem. Soc. (C), pp. 2274-2279 (1966).

Bozell, J.J. et al., "Catalytic Oxidation of Para-Substituted Phenols with Nitrogen Dioxide and Oxygen", Tetrahedron Letters, vol. 39, pp. 2261-2264 (1998).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Carey, F.A. et al, Section 5.6: "Leaving Group Effects", Advanced Organic Chemistry, Third Edition, Part A: Structure and Mechanisms, Plenum Press, publ., pp. 290-293 (1977).

Clewley, R.G. et al., "Formation of 4-Halo-4-nitrocyclohexa-2,5-dienones on Nitration of p-Halophenols and p-Halophenyl Acetates", Tetrahedron, vol. 45, No. 5, pp. 1299-1310 (1989).

Clewley, R.G. et al., "*ipso* Nitration in *p*-halophenyl ethers", Can J. Chem., vol. 67, pp. 1472-1479 (1989).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291-1293 (1976).

Fischer, A. et al., "Formation of Dienones on the Reaction of Cresols, Xylenols, and 2-naphthol with Nitrogen Dioxide: Observation of Keto Tautomers of Nitrophenols", Tetrahedron Letters, vol. 29, No. 16, pp. 1869-1872 (1988).

Gaude, D. et al., "Influence de la complexation sur la réactivité de nitrates d'halogènes", Can. J. Chem., vol. 67, pp. 104-108 (1989).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Greene, T.W. et al., Protective Groups in Organic Synthesis, Third Edition, John Wiley & Sons, Inc., publ., pp. xi-xii (table of contents) (1999).

Hara, S., "Ileal $Na^+$/bile acid cotransporter inhibitors", Drugs of the Future, vol. 24, No. 4, pp. 425-430 (1999).

Kajigaeshi, S. et al., "Bromination of Phenols by Use of Benzyltrimethylammonium Chlorobromate (1-)", Technol. Rep. Yamaguchi Univ., vol. 4, pp. 65-69 (1987).

Kajigaeshi, S. et al., "Bromination of Phenols by Use of Benzyltrimethylammonium Tribromide", Chemistry Letters, pp. 627-630 (1987).

Kajigaeshi, S. et al., "Chlorination of Phenols with Benzyltrimethylammonium Tetrachloroiodate", Chemistry Express, vol. 5, No. 3, pp. 141-144 (1990).

Kajigaeshi, S. et al., "Halogenation Using Quaternary Ammonium Polyhalides. IV. Selective Bromination of Phenols by Use of Tetraalkylammonium Tribromides", Bull. Chem. Soc. Jpn., vol. 60, pp. 4187-4189 (1987).

Kajigaeshi, S. et al., "Iodination of Phenols by Use of Benzyltrimethylammonium Dichlordodate(1-)", Chemistry Letters, pp. 2109-2112 (1987).

Kakinami, T. et al., "Halogenation Using Quarternary Ammonium Polyhalides. XX. Bromination of Phenols with Polymer-Bound Benzyltrimethylammonium Tribromide", Bull. Chem. Soc. Jpn., vol. 62, pp. 3373-3375 (1989).

Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press Inc., publ., Ruffolo, Jr., R.R. and Hollinger, M.A., eds., pp. 173-198 (1995).

Lemaire, M. et al., "Nitrocyclohexadienones: A New Class of Nitrating Agents", Tetrahedron, vol. 43, No. 5, pp. 835-844 (1987).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPARα) and PPAR-γ, etc.", Diabetes, vol. 47, pp. 1841-1847 (1998).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rodygin, M.Y. et al., "Bis[diemthylacetamide]hydrogen Dibromobromate—A New Brominating Agent", Zh. Org. Khim., pp. 1543-1544 (1992) (English translation).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sliskovic, D.R. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimbe: Treatment of Liproprotein Disorders, ACAT Inhibitor", Drugs of the Future, vol. 24, No. 1, pp. 9-15 (1999).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Takeda, K. et al., "Recessive Inheritance of Thyroid Hormone Resistance Caused by Complete Deletion of the Protein-Coding Region of the Thyroid Hormone Receptor-β Gene", Journal of Clinical Endocrinology and Metabolism, vol. 74, No. 1, pp. 49-55 (1992).

Xu, F., "Bromination of Phenols by Use of N-bromosuccinimide", Shanghai Keji Daxue Xuebao, vol. 12, pp. 72-76 (1989).

Yenes, S. et al., "A Study of the Reaction of Different Phenol Substrates with Nitric Oxide and Peroxynitrite", Tetrahedron, vol. 55, pp. 14111-14122 (1999).

Database CAPLUS on STN, AN 1968:95435. Yamanaka et al. "Chloromethylation of Phenol Derivaties", Yakugaku Zasshi 1968, vol. 88, No. 1, pp. 116-117, Abstract, lines 7-8.

Barbero et al., "1-Aryl-3,3-dialkyltriazenes: A Convenient Synthesis from Dry Arenediazonium o-Benzenedisulfonimides, etc.", Synthesis, 2001, No. 14, pp. 2180-2190, see p. 2188, Table 4, compounds 9k and 9l.

Baum et al., "Sulfonyl esters. 2. Carbon-Sulfur Bond Cleavage in Some Substitution Reactions of Nitrobenzenesulfonates", Canadian Journal of Chemistry, 1990, vol. 68, No. 8, pp. 1450-1454, see p. 1453, top, compound 7.

Grovenstein et at, JACS, vol. 84, 1962, pp. 212 to 220.

Kometani et al, Tetrahedron Letters, vol. 26 No. 17, 1985, pp. 2043-2046.

* cited by examiner

FIG. 1

PROCESS FOR THE PREPARATION OF ANILINE-DERIVED THYROID RECEPTOR LIGANDS

CROSS-REFERENCE TO RELATED APPLICATIONS

This application is a Divisional of U.S. patent application Ser. No. 10/936,062 filed Sep. 8, 2004, now abandoned which is a Divisional of U.S. patent application Ser. No. 10/273,268, now U.S. Pat. No. 6,806,381, which claims the benefit of U.S. Provisional Application Ser. No. 60/336,318 filed Nov. 2, 2001.

BACKGROUND OF THE INVENTION

The present invention relates to processes for the synthesis of organic molecules, specifically molecules that have activity as thyroid receptor ligands.

While the essential role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, the metabolic rate, body temperature, and mood, and influence serum-low density lipoprotein (LDL) levels. Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals, is limited by certain of the deleterious effects of thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor agonists could lead to specific therapies for these common disorders while avoiding the cardiovascular and other toxicities of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offer an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The $TR\alpha_1$, $TR\beta_1$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_1$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. This isoform may be especially important for development. Whereas many mutations in the TRβ gene have been found and lead to the syndrome of generalized resistance to thyroid hormone, mutations leading to impaired $TR\alpha_1$ function have not been found.

A growing body of data suggest that many or most effects of thyroid hormones on the heart, and in particular on the heart rate and rhythm, are mediated through the α-form of the $TR\alpha_1$ isoform, whereas most actions of the hormone such as on the liver, muscle and other tissues are mediated more through the β-forms of the receptor. Thus, a TRβ-selective agonist might not elicit the cardiac rhythm and rate influences of the hormones but would elicit many other actions of the hormones. It is believed that the α-form of the receptor is the major drive to heart rate for the following reasons:

1. tachycardia is very common in the syndrome of generalized resistance to thyroid hormone in which there are defective TRβ-forms, and high circulating levels of $T_4$ and $T_3$;
2. there was a tachycardia in the only described patient with a double deletion of the TRβ gene (Takeda et al., J. Clin. Endrocrinol. & Metab. 1992, Vol. 74, p. 49);
3. a double knockout TRα gene (but not β-gene) in the mouse has a slower pulse than control mice; and,
4. western blot analysis of human myocardial TRs show presence of the $TR\alpha_1$, $TR\alpha_2$ and $TR\beta_2$ proteins, but not $TR\beta_1$.

If these indications are correct, then a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and, (6) osteoporosis in combination with a bone resorption inhibitor.

Thyroid receptor ligands of the formula I, below, have previously been synthesized by several methods including the method summarized in Scheme A. (See U.S. patent application Ser. No. 09/761,050, filed Jan. 16, 2001.) The group G represents any group appropriate for protecting a hydroxyl moiety. The group Z represents a leaving group, such as a halogen. Examples of appropriate protecting groups G can be found, for example, in T. W. Greene & P. G. M. Wuts, "Protecting Groups in Organic Synthesis", 3$^{rd}$ Edition, Wiley, 1999.

wherein:
R¹ represents halogen, trifluoromethyl, an alkyl group of 1 to 6 carbons, or a cycloalkyl group of 3 to 7 carbons;
R² and R³ are the same or different and represent hydrogen, halogen, an alkyl group of 1 to 4 carbons, or a cycloalkyl group of 3 to 6 carbons, at least one of R² and R³ being other than hydrogen;
R⁴ represents hydrogen or a lower alkyl group;
R⁵ represents a carboxylic acid or an alkyl ester thereof; and
Y represents —(CH₂)ₙ— where n is an integer from 1 to 5, or a cis- or trans-ethylene group —CH═CH—; and all stereoisomers thereof, prodrug esters thereof, and pharmaceutically acceptable salts thereof.

Compounds of formula I may be synthesized by reacting a compound of formula III with a phenol of formula A, wherein G is a protecting group, in the presence of a base to produce a compound of formula IV, wherein R¹, R², R³, and R⁴ are as defined above;

III

A

IV deprotecting the compound of formula IV to form a compound of formula V;

V reducing the compound of formula V to produce a compound of formula VI;

This route is not optimal, however, due to the exothermicity of the formation of the iodonium triflate salt which is an unisolated intermediate in the synthesis depicted in Scheme A. In addition, the isolated, bis-phenyl iodonium salt is an intractable gummy solid at room temperature, and the yield of the formation reaction is unpredictable. Further, the coupling reaction to form the mixed ether from the iodonium salt is not well adapted to commercial practice, because it takes place over an extended period of time, it requires unusual provisions to exclude light, and its yield is also unpredictable.

Accordingly, there is a need for improved processes for the preparation of thyroid receptor ligands, especially for processes that improve upon the safety and economic feasibility of the processes known in the art.

SUMMARY OF THE INVENTION

The present invention relates to the synthesis of compounds that have activity as thyroid receptor ligands, specifically compounds of formula I

VI reacting the compound of formula VI with a compound of the formula $XC(O)YR^5$, wherein X represents OH or a halogen and $R^5$ is a carboxylic acid alkyl ester, in the presence of a base, to produce a compound of formula I wherein $R^5$ is a carboxylic acid alkyl ester; and optionally de-esterifying the compound of formula I wherein $R^5$ is a carboxylic acid alkyl ester to produce a compound of formula I wherein $R^5$ is a carboxylic acid.

Also provided by the present invention are compounds that are novel starting materials of the above process having the formulae IIA and IIIA

IIA

IIIA wherein
$R^2$ and $R^3$ independently represent bromo, chloro, or methyl;
$R^4$ represents hydrogen or methyl; and
L represents mesyl, tosyl, p-nitrobenzenesulfonyl, trihaloacetate, or triflate.

The present invention also provides compounds of the formulae A, A-I, and A-II

A

A-I

A-II wherein M is a metal and G and $R^1$ are as defined above. In compounds of formula A, however, when G is a methyl group, $R^1$ is not a bromo, chloro, iodo, t-butyl, cyclohexyl, cyclopentyl, or isopropyl group.

Also provided by the present invention is a process for synthesizing a phenol of formula A, above, by reacting an aldehyde of formula A-I, above, with $M^+HSO_3^-$ wherein M is a metal to form a sulfonate of formula A-II, above. The sulfonate of formula A-II is reacted with an oxidant in the presence of a proton source to form the phenol of formula A.

DESCRIPTION OF THE PREFERRED EMBODIMENTS

The following definitions apply to the terms as used throughout this specification, unless otherwise limited in specific instances.

The term "thyroid receptor ligand" as used herein, is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "lower alkyl", "alkyl" or "alk" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl. Each alkyl group may be optionally substituted with 1 to 4 substituents which may include alkyl, alkenyl, alkynyl, aryl, cycloalkyl, halogen, heteroaryl, hydroxy, cyano, nitro, amino and/or carboxyl or alkyl ester thereof.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, hydroxy, amino, nitro, cyano and/or carboxyl or an alkyl ester thereof.

The term "heteroaryl" or "heteroaromatic moiety" as used herein alone or as a part of another group refers to a 5- or 6-membered aromatic ring which includes 1, 2, 3, or 4 heteroatoms, one of which must be a nitrogen atom; the other heteroatoms when present may be nitrogen, oxygen or sulfur, and such rings may be fused to another aryl or heteroaryl ring.

The heteroaryl groups may include one or more N-oxides. The heteroaryl group may optionally include 1 to 4 substituents such as aryl, alkyl, alkenyl, alkynyl, cycloalkyl, hydroxy, cyano, nitro, amino and/or carboxyl, or an alkyl ester thereof.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted in the same manner as that described for alkyl groups.

Unless otherwise indicated, the term "lower alkynyl" or "alkynyl" as used herein by itself or as part of another group refers to straight or branched chain radicals of 2 to 12 carbons, preferably 2 to 8 carbons, in the normal chain; which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, which may be substituted in the same manner as that described for alkyl groups.

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 6 carbons, forming the ring, which includes cyclopropyl, cyclobutyl, cyclopentyl, cyclohexyl, cycloheptyl, cyclopentenyl and cyclohexenyl, which may be substituted in the same manner as that described for alkyl groups.

The term "halogen" or "halo" as used herein alone or as part of another group refers to fluorine, chlorine, bromine, and iodine, with chlorine or bromine being preferred.

The term "metal" as used herein refers to an element that can exist as a positive ion in solution. Suitable metals include alkali metals, transition metals, lanthanides, and actinides. Alkali metals are preferred. Lithium, sodium, and potassium are the most preferred metals.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such.

The divalent linking group represented by Y may be an alkylene group —$(CH_2)_n$— that includes 1 to 5 carbons in the normal chain, and may also include 1, 2, or 3 alkyl substituents.

Examples of $(CH_2)_n$ groups include —$CH_2$—, —$CH_2CH_2$—, —$CH_2CH_2CH_2$—, —$CH_2CH_2CH_2CH_2$— $CH_2CH_2C(CH_3)_2CH_2$—, —$CH_2CH_2CH(CH_2CH_3)CH_2$— $CH_2CH_2CH(CH_2CH_3)CH_2CH(CH_3)$—, —$C(CH_3)$ $(CH_2CH_3)CH_2CH_2$—, —$CH(CH_3)$—, —$CH(CH_2CH_3)$—, —$CH(CH_3)CH_2CH(CH_2CH_3)CH_2$—.

Alternatively, Y may represent a cis- or trans-alkylene group —CH=CH— which may be substituted as described above.

The compounds of formula I may be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4) alkyl or arylsulfonic acids which are unsubstituted or substituted, for example by halogen, for example methanesulfonic acid or p-toluenesulfonic acid.

Corresponding acid addition salts can also be formed having, if desired, an additional basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di-, or tri-lower alkylamine, for example ethyl, t-butyl, diethyl, diisopropyl, triethyl, tributyl or dimethyl-propylamine, or a mono, di, or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which include a basic group include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Preferred compounds of formula I are those wherein

Y represents —$(CH_2)_n$— where n is 1 or 2;
$R^1$ represents halogen, trifluoromethyl, an alkyl group of 1 to 6 carbons, or a cycloalkyl group of 3 to 7 carbons;
$R^2$ and $R^3$ independently represent bromo, chloro, or methyl;
$R^4$ represents hydrogen or methyl; and
$R^5$ represents carboxyl.

More preferred compounds of formula I are those wherein

Y represents —$(CH_2)_n$— where n is 1;
$R^1$ represents halogen, trifluoromethyl, an alkyl group of 1 to 6 carbons, or a cycloalkyl group of 3 to 7 carbons, most preferred being isopropyl;
$R^2$ and $R^3$ independently represent bromo or chloro;
$R^4$ represents hydrogen or methyl; and
$R^5$ represents carboxyl.

Compounds of formula I that can be prepared by the methods of the invention include the following:

N-[3,5-dibromo-4-(4-hydroxy-3-isopropyl-phenoxy)-phenyl]-malonamic acid;

N-[3,5-dibromo-4-(4-hydroxy-3-isopropyl-phenoxy)-2-methyl-phenyl]-malonamic acid;

N-[3,5-dibromo-4-(4-hydroxy-3-isopropyl-phenoxy)-phenyl]-succinamic acid;

N-[3,5-dichloro-4-(4-hydroxy-3-isopropyl-phenoxy)-phenyl]-malonamic acid;

N-[3,5-dichloro-4-(4-hydroxy-3-isopropyl-phenoxy)-2-methyl-phenyl]-malonamic acid; and N-[3,5-dichloro-4-(4-hydroxy-3-isopropyl-phenoxy)-phenyl]-succinamic acid, or alkyl esters thereof, such as the methyl or ethyl ester.

The most preferred compounds of the invention are:

N-[3,5-dibromo-4-(4-hydroxy-3-isopropyl-phenoxy)-phenyl]-malonamic acid; and

N-[3,5-dichloro-4-(4-hydroxy-3-isopropyl-phenoxy)-phenyl]-malonamic acid, or alkyl esters thereof, such as the methyl or ethyl ester.

Preferred compounds of formula IIA include trifluoro-methanesulfonic acid 2,6-dibromo-4-nitrophenyl ester, trifluoro-methanesulfonic acid 2,6-dibromo-3-methyl-4-nitrophenyl ester, trifluoro-methanesulfonic acid 2,6-dichloro-4-nitrophenyl ester, and trifluoro-methanesulfonic acid 2,6-dichloro-3-methyl-4-nitrophenyl ester.

A more preferred compound of formula IIA is trifluoro-methanesulfonic acid 2,6-dibromo-4-nitrophenyl ester.

Preferred compounds of formula IIIA include 1,3-dibromo-2-iodo-5-nitrobenzene, 1,3-dibromo-2-iodo-4-methyl-5-nitrobenzene, 1,3-dichloro-2-iodo-5-nitrobenzene, and 1,3-dichloro-2-iodo-4-methyl-5-nitrobenzene.

A more preferred compound of formula IIIA is 1,3-dibromo-2-iodo-5-nitrobenzene.

Preferred compounds of formulae A, A-I, and A-II for practicing the present invention are those in which $R^1$ represents halogen, trifluoromethyl, an alkyl group of 1 to 6 carbons, or a cycloalkyl group of 3 to 7 carbons.

More preferred compounds of formulae A, A-I, and A-II are those in which $R^1$ represents halogen, trifluoromethyl, an alkyl group of 1 to 6 carbons, or a cycloalkyl group of 3 to 7 carbons, most preferred being isopropyl.

The most preferred compound of formula A-I is 3-isopropyl-4-methoxybenzaldehyde. The most preferred compound of formula A-II is hydroxy-(3-isopropyl-4-methoxyphenyl)methanesulfonic acid, sodium salt. The most preferred phenol of formula A is 3-isopropyl-4-methoxyphenol.

All stereoisomers of the compounds of formula I are contemplated, either in admixture or in pure or substantially pure form. The compounds of formula I can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods, for example, chromatographic or fractional crystallization.

The compounds of formula I may be prepared by the exemplary processes described in the following reaction schemes. Exemplary reagents and procedures for these reactions appear hereinafter and in the working examples. Protection and deprotection in the Schemes herein may be carried out by procedures generally known in the art (see, for example, Greene & Wuts).

Scheme 1 sets forth an improved method of synthesizing compounds of formula I.

In scheme 1, $R^1$, $R^2$, $R^3$, and $R^4$ are as defined above, M represents a metal, the group G represents any group appropriate for protecting a hydroxyl moiety, and the group —OL represents a leaving group. Examples of suitable protecting groups G can be found in Green and Wuts, for example. Examples of suitable leaving groups L can be found in Carey, F. A. and Sundberg, R. J., *Advanced Organic Chemistry* (1977, Plenum Press, New York), Part A, Section 5.6, for example.

Preferred protecting groups include, e.g., substituted or unsubstituted alkyl, methoxymethyl (MOM), carboxybenzyl (CBz), benzyloxymethyl (BOM), 2-(trimethylsilyl)ethoxymethyl (SEM), aryl thiomethyl (MTM), tetrahydropyranyl, methyl 2-propenyl ether, ethyl vinyl ether, triphenylmethyl (trityl) and other triarylmethyl groups, esters, carbonates, phosphinates, sulfonates, and silyl groups.

More preferred protecting groups are alkyl groups.

The most preferred protecting groups are alkyl groups containing 1 to 6 carbons, especially methyl groups.

Preferred leaving groups include, e.g., tri-haloacetates and sulfonate esters.

More preferred leaving groups are trihalo-methylsulfonate, methylsulfonate (mesyl), p-nitrobenzenesulfonate, p-toluenesulfonate (tosyl), and trihaloacetate groups.

The most preferred leaving groups are trifluoromethylsulfonate (triflate) groups.

Phenols of formula A may be synthesized by methods known in the art. See, for example, Blank, B., *J. Med. Chem.*, 1963, 6, 554, and Bowman et al., *J. Chem. Soc. C*, 1966, 2274. Phenols of formula A may also be synthesized by the novel method of the present invention, wherein an aldehyde of formula A-I is reacted with about 2 to 4 equivalents of a sulfite reagent, such as an sodium sulfite or an alkali hydrogen sulfite, at about 200 to 30° C. to produce a sulfonate of formula A-II. Preferably, about 2.25 to 2.75 equivalents of sulfite reagent are used, the preferred sulfite reagent being sodium sulfite.

The phenol of formula A is formed by reacting the sulfonate of formula A-II with an oxidant, in the presence of a proton source. Preferably, about 1 to 2 equivalents of protons and about 3 to 5 equivalents of oxidant are used.

Suitable oxidants for use in the synthesis of Phenol A include, e.g., peroxybenzoic acids, alkali metal monoperoxophthalates, hydrogen peroxide optionally catalyzed by MeReO$_3$, oxygen in the presence of a copper species, $H_3PO_5$, and oxone. More preferably, the oxidant is hydrogen peroxide.

Preferably, the proton source is a protic acid. More preferably, the proton source is p-toluenesulfonic acid.

Phenol B may be synthesized by well-known methods from commercially available starting materials. See, for example, Yenes, S. et al., *Tetrahedron*, 1999, 55, 14111; Bozell, J. et al., *Tet. Lett.*, 1998, 39, 2261; Fischer, A. et al., *Tet. Lett.*, 1988, 29, 1869; Rodygin, M. et al., *zh. Org. Khim.*, 1992, 28, 1926; Xu, F. et al., *Shanghai Keji Daxue Xuebao*, 1989, 12, 72; Clewly, R. et al., *Can. J. Chem.*, 1989, 67, 1472; Kajigaeshi, S. et al., *Bull. Chem. Soc. Japan*, 1987, 60, 4187; Kajigaeshi S. et al., *Chem. Lett.*, 1987, 4, 627; Lemaire, M. et al, *Tetrahedron*, 1987, 43, 835; Fujita, S. et al., *JP* 03291241, 1991; Clewly, R. et al., *Tetrahedron*, 1989, 45, 1299; Kajigaeshi, S. et al., *Chem. Express*, 1990, 5, 141; Kakinami, T. et al., *Bull. Chem. Soc. Japan*, 1989, 62, 3373; Kajigaeshi, S. et al., *Technol. Rep. Yamaguchi Univ.*, 1987, 4, 65; Gaude D. et al., *Can. J. Chem.*, 1989, 67, 104; Kajigaeshi, S. et al., *Chem. Lett.*, 1987, 2109. Certain Phenol B compounds are also commercially available from the Aldrich Company, for example.

Compounds of formula III are synthesized from compounds of formula II by iodination. Iodination reagents include, e.g., alkali metal iodides and tetraalkylammonium iodides. Preferred iodination reagents include, e.g., sodium iodide and potassium iodide. Preferably, the iodination agent is present in about 1-fold to 10-fold excess. Preferably, the iodination is carried out at 800 to 110° C. Preferably, the solvent is acetone, methyl ethyl ketone (MEK), methyl isobutyl ketone (MIBK), toluene, hexamethylphosphorustriamide (HMPA), dimethyl formamide (DMF), or a higher-boiling acetate. More preferably, the iodination is carried out by reacting the compound of formula II with 3- to 5-fold excess NaI or KI in DMF, MEK or MIBK at a temperature of about 75° to 100° C.

The coupling reaction to form the mixed ether of formula IV from the compound of formula III and phenol A is conducted in the presence of a base. Preferred bases include, e.g., alkyl lithiums, lithium diisopropylamine, Grignard reagents, alkali metal hydrides, alkali metal carbonates, alkali metal hydroxides, and alkali metal alkoxides. Preferred solvents include THF, 1,2-dimethoxyethane, 1,1-dimethoxyethane, dimethyl sulfoxide (DMSO), and toluene. Preferably, about 1.1 to 1.5 equivalents of base are used. Preferably, the reaction temperature is between about −78° and 30° C. More preferably, the coupling reaction is performed in toluene/DMF or toluene/THF or DMF at room temperature using potassium hexamethyldisilazide (KHMDS), potassium t-butoxide, potassium t-pentoxide, LiHMDS, or NaHMDS as the base.

The deprotection of the protected hydroxyl group of compound IV may be carried out at reaction temperatures below room temperature. Preferred deprotecting agents include, e.g., trialkylsilyl halides, mercaptans, boron halides, magnesium halides, aluminum halides, hydrogen over palladium catalyst, or iron halides. Preferably, the reaction temperature is maintained between about 0° to 15° C. Preferably, the deprotection reaction is quenched with at least about 4 molar equivalents of methanol. More preferably, the deprotecting agent is a trialkylsilyl halide or $BBr_3$.

Reducing agents and conditions suitable for use in reducing the formula V compound include, e.g., elemental metals such as Fe and Na; hydrogen catalyzed by nickel, palladium or platinum; alkali metal borohydrides; magnesium-mediated reductions; iron carbonyls; iron sulfate mediated reductions; iron and HCl; sodium hydrogen sulfite; sodium dithionite; tin and tin halide mediated reductions; and alkali metal sulfides and polysulfides. Preferred reducing agents include, e.g., sodium hydrogen sulfite, sodium dithionite, or iron and HCl. Preferably, about 4 to 6 equivalents of reducing agent are used. Preferably, the reaction temperature is maintained between about 25° to 50° C. More preferably, the reducing agent is sodium dithionite, and the reaction is carried out over about 1 h in THF/$H_2O$ at about 50° C.

Formula VI compounds may be converted into formula I compounds wherein $R^5$ is an alkyl ester group by reaction with a compound of formula $XC(O)YR^5$, wherein X and Y are as defined above, under basic conditions. Preferred bases are alkali and alkaline earth metal hydroxides and alkoxides, alkyl amines, and substituted alkyl amines. Preferred compounds of formula $XC(O)YR^5$ are alkyl and malonyl halides. Preferably, the reaction temperature is maintained between about 0° and 5° C. Preferably, about 1 equivalent or a slight excess of base is used. Preferably, about 50% to 100% excess of the compound of formula $XC(O)YR^5$ is used. More preferably, $XC(O)YR^5$ is ethyl or methyl malonyl chloride and the reaction is carried out at a temperature around 0° C. under basic conditions, using NaOH in t-butyl methyl ether (TBME).

In the above Scheme 1, the deprotection of the phenol hydroxyl group of compound IV to form the compound of formula V is depicted as being performed before the reduction of the nitro group to form the compound of formula VI. The order in which these two reactions are performed may be reversed, however. When the order is thus reversed, a compound of formula VA is formed by the reduction.

VA

The compound of formula VA is readily deprotected to form the compound of formula VI. It is preferred, however, to carry out the deprotection before the reduction.

Compounds of formula I wherein $R^5$ is an alkyl ester may be de-esterified by hydrolysis under acidic or basic conditions to form compounds of formula I wherein $R^5$ is a carboxylic acid. Examples of suitable de-esterifying agents include, e.g., enzymes; hydrogen over catalytic palladium; lithium and ammonia; zinc; alkali metal hydroxides and alkoxides; alkaline earth metal hydroxides and alkoxides; sodium sulfide; KSCN; thioethers in combination with Lewis acids; anions of alkyl thiols or selenols; trialkyl silyl halides; zinc dichloride; mercury (II) acetate; and strong protic acids.

Preferred hydrolysis reagents and conditions include, e.g., an alkali metal hydroxide in the presence of an ether such as tetrahydrofuran or tert-butyl methyl ether. Most preferably, the hydrolysis is carried out in situ by the addition of approximately 1.5 to 2 molar equivalents of NaOH to the reaction mixture at a temperature around 0° C. after the reaction of compound VI with $XC(O)YR^5$ wherein X and Y are as previously defined and $R^5$ is an alkyl ester group is observed to be essentially complete.

The compounds made by the processes of the invention are agonists that are preferably selective for the thyroid hormone receptor-beta, and as such are useful in the treatment of obesity, hypercholesterolemia and atherosclerosis by lowering of serum LDL levels, alone or optionally in combination with a lipid modulating drug such as an HMG CoA reductase inhibitor, fibrate, MTP inhibitor, squalene synthetase inhibitor and/or other hypolipidemic agent and/or optionally in combination with an antidiabetic agent; useful in the amelioration of depression, alone or optionally in combination with an antidepressant such as fluoxetine and desipramine; and useful in the stimulation of bone formation to treat osteoporosis, alone or optionally in combination with any known bone resorption inhibitor such as alendronate sodium.

In addition, the compounds of the invention may be useful as replacement therapy in elderly patients with hypothyroidism or subclinical hypothyroidism who are at risk for cardiovascular complications, in the treatment of the elderly to provide a sense of well-being, and in the treatment of non-toxic goiter; in the management of papillary or follicular thyroid cancer (alone or with T4); in the treatment of skin disorders such as psoriasis; and in the treatment of glaucoma, cardiovascular disease such as in the prevention or treatment of atherosclerosis, and congestive heart failure.

The compounds made by the processes of the invention may be employed alone or in combination with an appetite suppressant such as sibutramine, and/or in combination with anti-obesity agents such as orlistat, and/or in combination with a β3 agonist, for treating obesity.

The compounds made by the processes of the invention may also be used to treat skin disorders or diseases involving dermal atrophy such as glucocorticoid induced dermal atrophy, including restoration of dermal atrophy induced by topical glucocorticoids, the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichthyosis, acne, psoriasis, Dernier's disease, eczema, atopic dermatitis, chloracne, pityriasis and skin scarring.

In treating skin disorders or diseases as described above, the compounds made by the processes of the invention may be used alone or optionally in combination with a retinoid such as tretinoin or a vitamin D analog, employing amounts as disclosed in the PDR.

The hypolipidemic agent which may be optionally employed in combination with the compounds of formula I may include thiazolidinediones, MTP inhibitors, HMG CoA reductase inhibitors, squalene synthetase inhibitors, fibric acid derivatives, ACAT inhibitors, cholesterol absorption inhibitors, ileal Na+/bile acid cotransporter inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and 5,962,440. Preferred are each of the preferred MTP inhibitors disclosed in each of the above patents and applications.

Most preferred MTP inhibitors to be employed with the compounds made by the processes of the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl)butyl]-N-(2,2,2-trifluoroethyl)-9H-fluorene-9-carboxamide, formula VII.

VII

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use with compounds of formula I are disclosed in GB 2205837.

The squalene synthetase inhibitors suitable for use with compounds of formula I include, but are not limited to, α-phosphonosulfonates disclosed in U.S. Pat. No. 5,712,396, those disclosed by Biller et al., J. Med. Chem., 1988, Vol. 31, No. 10, pp 1869-1871, including isoprenoid (phosphinylmethyl)phosphonates as well as other squalene synthetase inhibitors as disclosed in U.S. Pat. Nos. 4,871,721 and 4,924 024 and in Biller et al., Current Pharmaceutical Design, 2, 1-40 (1996).

In addition, other squalene synthetase inhibitors suitable for use with compounds of formula I include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J. Am. Chem. Soc., 1987, 109, 5544 and cyclopropanes reported by Capson, T. L., PhD dissertation, June, 1987, Dept. Med. Chem. Univ. of Utah, Abstract, Table of Contents, pp 16, 17, 40-43, 48-51, Summary.

Other hypolipidemic agents suitable for use with compounds of formula I include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipal and DEAE-Sephadex (Secholex™, Policexide™, as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in Drugs of the Future 24, 9-15 (1999), (Avasimibe); Nicolosi et al., Atherosclerosis (Shannon, Ireland) 1998, 137(1), 77-85; Ghiselli, Giancarlo, Cardiovasc. Drug Rev. 1998, 16(1), 16-30; Smith, C., et al., Bioorg. Med. Chem. Lett. 1996, 6(1), 47-50; Krause et al., Editor(s): Ruffolo et al., Inflammation: Mediators Pathways 1995, 173-98, Publisher: CRC Press, Boca Raton, Fla.; Sliskovic et al., Curr. Med. Chem. 1994, 1(3), 204-25; Stout et al., Chemtracts: Org. Chem. 1995, 8(6), 359-62.

The hypolipidemic agent may be a cholesterol absorption inhibitor preferably Schering-Plough's SCH48461 as well as those disclosed in Atherosclerosis 115, 45-63 (1995) and J. Med. Chem. 41, 973 (1998).

The hypolipidemic agent may be an ileal Na$^+$/bile acid cotransporter inhibitor such as disclosed in Drugs of the Future, 24, 425-430 (1999). Preferred hypolipidemic agents are pravastatin, lovastatin, simvastatin, atorvastatin, fluvastatin and cerivastatin.

The amounts and dosages employed will be as indicated in the Physician's Desk Reference (PDR) and/or in the patents set out above.

The compounds of formula I will be employed in a weight ratio to the hypolypidemic agent, the antidepressant, and/or bone resorption inhibitor and/or appetite suppressant (where present), within the range from about 500:1 to about 0.005:1, preferably from about 300:1 to about 0.01:1.

The antidiabetic agent which may be optionally employed in combination with compounds of formula I may include biguanides, sulfonyl ureas, glucosidase inhibitors, thiazolidinediones and/or aP2 inhibitors and/or PPAR α agonists, PPAR γ agonists or PPAR α/γ dual agonists, and/or SGLT2 inhibitors, or meglitinide.

The antidiabetic agent may be an oral antihyperglycemic agent, preferably a biguanide such as metformin or phenformin or salts thereof.

Where the antidiabetic agent is a biguanide, the compounds of formula I will be employed in a weight ratio to biguanide within the range from about 0.01:1 to about 100:1, preferably from about 0.5:1 to about 2:1.

The antidiabetic agent may also preferably be a sulfonylurea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred.

The compounds of formula I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in a separate oral dosage form.

The compounds of formula I will be employed in a weight ratio to the glucosidase inhibitor within the range from about 0.01:1 to about 100:1, preferably from about 0.5:1 to about 50:1.

The compounds of formula I may be employed in combination with a thiazolidinedione oral anti-diabetic agent or other insulin sensitizers (which has an insulin sensitivity effect in NIDDM patients) such as troglitazone (Warner-Lambert's Rezulin™, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GI-262570, englitazone (CP-68722, Pfizer), or darglitazone (CP-86325, Pfizer).

The compounds of formula I will be employed in a weight ratio to the thiazolidinedione in an amount within the range from about 0.01:1 to about 100:1, preferably from about 0.5:1 to about 5:1.

The sulfonylurea and thiazolidinedione in amounts of less than about 150 mg oral antidiabetic agent may be incorporated in a single tablet with the compounds of structure I.

The compounds of formula I may also be employed in combination with a non-oral antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices.

Where present, metformin, the sulfonylureas, such as glyburide, glimepiride, glipyride, glipizide, chlorpropamide and gliclazide and the glucosidase inhibitors acarbose or miglitol or insulin may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day, which may be administered in single or divided doses one to four times per day.

Where present insulin may be employed in formulations, amounts and dosing as indicated by the Physician's Desk Reference (PDR).

Where present GLP-1 peptides may be administered in oral buccal formulations, by nasal administration or parenterally as described in U.S. Pat. Nos. 5,346,701 (TheraTech), 5,614,492 and 5,631,224.

The antidiabetic agent may also be a PPAR α/γ dual agonist such as disclosed by Murakami et al., "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998).

The antidiabetic agent may be an aP2 inhibitor such as disclosed in U.S. application Ser. No. 09/391,053, filed Sep. 7, 1999, and U.S. provisional application No. 60/127,745, filed Apr. 5, 1999, employing dosages as set out herein.

The antidiabetic agent may be an SGLT2 inhibitor such as disclosed in U.S. provisional application 60/158,773, filed Oct. 12, 1999.

The compounds of formula I will be employed in a weight ratio to the PPAR α agonist, PPAR γ agonist, PPAR α/γ dual agonists, SGLT2 inhibitor and/or aP2 inhibitor within the range from about 0.01:1 to about 100:1, preferably from about 0.5:1 to about 5:1.

The dose administered must be carefully adjusted according to age, weight and condition of the patient, as well as the route of administration, dosage form and regimen and the desired result.

The dosages and formulations for the hypolipidemic agent and antidiabetic agent will be as disclosed in the various patents and applications discussed above and in the Physicians' Desk Reference.

The dosages and formulations for the other hypolipidemic agent, antidepressant, bone resorption inhibitor, appetite suppressant and anti-obesity agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The compounds of formula I and the hypolipidemic agent, antidepressant or bone resorption inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The compounds of formula I can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, ointment, hydrophilic ointment, cream, lotion, solution or suspension or in other type carrier materials such as transdermal devices, iontophoretic devices, rectal suppositories, inhalant devices and the like. The composition or carrier will contain about 5 to about 500 mg per unit of dosage of a compound of formula I. The active substances may be compounded in a conventional matter with a physiologically acceptable vehicle or carrier, excipient, binder, preservative, stabilizer, or flavor, as called for by accepted pharmaceutical practice.

The following examples are provided to describe the invention in further detail. These examples are intended to illustrate and not to limit the invention. All temperatures are given in centigrade degrees (° C.) unless otherwise noted.

Example 1

Preparation of 1-isopropyl-2-methoxybenzene

A 22 L three-necked round bottom flask equipped with mechanical stirring was charged with KOH (1154 g, 20.56 moles), tetrabutylammonium hydrogen sulfate (140 g, 0.411 mole), and deionized water (5.6 L). The mixture was cooled to a temperature of approximately 20° C. to 25° C. Methylene chloride (5.6 L) was added to the flask, then 2-isopropylphenol (590 g, 4.33 moles). The mixture was stirred for 0.5 h before iodomethane (741 g, 5.22 moles) was added. The stirring was continued at room temperature until the reaction was observed to be complete by HPLC, typically after approximately 5 h. Stirring was discontinued and the reaction mixture was allowed to settle into aqueous and organic layers, which were then separated. Triethylamine (185 mL, 1.33 moles) was added to the organic phase with stirring for at least 15 min. Solvent was then removed by vacuum distillation to afford a white solid. Cyclohexane (4l) was added to the white solid, which was filtered and washed with further cyclohexane to remove the reaction product as a solvate. The cyclohexane solution was washed with aqueous HCl (2N), then half-saturated aqueous NaCl, and finally saturated aqueous NaCl. The cyclohexane was removed by vacuum distillation to afford 1-isopropyl-2-methoxybenzene as a light yellow oil of medium viscosity (612 g, 94% yield).

Example 2

Preparation of 3-isopropyl-4-methoxybenzaldehyde

A 5 L three-necked round bottom flask was equipped with mechanical agitation and provided with an inert gas blanket.

The flask was charged with 1-isopropyl-2-methoxybenzene (859 g, 5.85 moles) and dimethylformamide (1584 mL, 20.46 moles), and the mixture was heated to 80° C. Phosphorus oxychloride (2690 g, 17.54 moles) was added to the reaction mixture over approximately 3 h while maintaining the temperature of the reaction mixture between 80° C. and 90° C. The addition of $POCl_3$ caused an immediate color change with continuous darkening over the course of the reaction. The reaction mixture was maintained at 80° C. for approximately 16 h, then checked by HPLC for presence of unreacted starting materials. The reaction mixture was quenched by slow addition over approximately 2 h to icewater (8 kg total, 5 kg ice); alternatively the reaction mixture was added over approximately 3 h to deionized water (10 L) in a jacketed 30 L reactor whose cooling bath was maintained between 0° and 5° C. Ethyl acetate (12 L) was added to the quenched reaction with stirring. After settling, the layers were separated, and the aqueous layer was washed with additional ethyl acetate (4 L). The combined organic layers were washed with saturated aqueous sodium bicarbonate solution (4 L) and saturated aqueous sodium chloride (4 L). The ethyl acetate was removed by vacuum distillation to yield 3-isopropyl-4-methoxybenzaldehyde (881 g, 86.5%).

Example 3

Preparation of hydroxy-(3-isopropyl-4-methoxyphenyl)methanesulfonic acid, sodium salt A 22 L three-necked round bottom flask equipped with mechanical agitation was charged with 3-isopropyl-4-methoxybenzaldehyde (880 g, 4.94 moles), THF (4650 mL), and cyclohexane (3740 mL) at room temperature. To this mixture was added, with stirring, an aqueous solution of sodium bisulfite (1310 g, 12.56 moles, in 4360 mL of deionized water). The reaction mixture was stirred overnight at room temperature. The reaction product was removed by filtration, washed liberally with cyclohexane:THF (3:1) and dried overnight by evaporation under air flow at room temperature to yield hydroxy-(3-isopropyl-4-methoxyphenyl)methanesulfonic acid as the sodium salt (1302 g, 93.4%).

Example 4

Preparation of 3-isopropyl-4-methoxyphenol

A 22 L three-necked round bottom flask equipped with mechanical agitation was charged with hydroxy-(3-isopropyl-4-methoxyphenyl)methanesulfonic acid, sodium salt (1300 g, 4.61 moles), p-toluenesulfonic acid monohydrate (908 g, 4.77 moles), and methanol (10.4 L), and the mixture was cooled to 0° to 5OC. Hydrogen peroxide (30% aqueous, 1.625 L, 16.12 moles) was added slowly to the reaction mixture over about 2 h. The reaction mixture was stirred overnight and allowed to return to room temperature. The completeness of the reaction was assayed by HPLC; if the reaction was incomplete, further hydrogen peroxide was added to the reaction mixture. The reaction mixture was cooled once more to 0° to 5° C. and then quenched by addition of an aqueous slurry of sodium dithionite (1860 g, 10.68 moles, stirred 1 h at room temperature in 6.5 L deionized water). After stirring at least 0.5 h, the reaction mixture was filtered, and the white solids were washed with ethyl acetate (8 L). The ethyl acetate and the aqueous filtrate were combined, agitated, and allowed to separate. Cyclohexane was added if necessary to facilitate separation. The organic phase was washed with sodium bicarbonate (4 L, 10% aqueous solution), then with saturated aqueous sodium chloride solution (4 L). The solvent was removed by vacuum distillation to afford 3-isopropyl-4-methoxyphenol (510 g, 66.7%).

Example 5

Preparation of Trifluoromethanesulfonic acid 2,6-dibromo-4-nitrophenyl ester

A 12 L jacketed vessel equipped with a mechanical stirrer and nitrogen inlet adapter was charged with dichloromethane (3.2 L) and 2,5-dibromo-4-nitrophenol (800 g, 2.69 moles). The reaction mixture was cooled to 0° C. and sparged with nitrogen gas. Pyridine (0.436 L, 3.23 moles) was introduced via addition funnel while the temperature of the reaction mixture was maintained below 8° C. The reaction mixture was stirred at 0° C. for 5 min, then a solution of triflic anhydride (0.544 L, 3.23 moles) in dichloromethane (0.400 L) was added via addition funnel while maintaining the reaction temperature below 10° C. The reaction mixture was warmed to room temperature, stirred 30 min, and monitored periodically by HPLC. After the reaction had run to completion, aqueous hydrochloric acid (1N, 1.6 L) was added to the reaction mixture dropwise with stirring. The reaction temperature was maintained below 35° C. during the addition of the acid. The reaction mixture was allowed to settle into layers, and the organic phase was separated and washed first with saturated aqueous sodium bicarbonate (0.8 L), then with saturated aqueous sodium chloride (0.8 L). The organic phase was concentrated by rotary evaporation under vacuum at 40° C., then dried overnight under vacuum to yield trifluoromethane sulfonic acid 2,6-dibromo-4-nitrophenyl ester (1140 g, 99.1%).

Example 6

Preparation of 1,3-dibromo-2-iodo-5-nitrobenzene

Dimethylformamide (4 L) and trifluoromethane sulfonic acid 2,6-dibromo-4-nitrophenyl ester (1135 g, 2.65 moles) were charged into a 22 L jacketed vessel equipped with a mechanical stirrer, a condenser, and a nitrogen purge. Sodium iodide (1595 g, 10.64 moles) was added to the reaction mixture in portions while maintaining the reaction temperature below 25° C. The reaction mixture was then heated to 100° C. and monitored for completion by HPLC. Upon completion, the reaction mixture was cooled to 0° C. Water (4 L) was added while maintaining the temperature below 14° C. The reaction mixture was stirred for 30 min, then filtered and washed with water (1.5 L). The resultant solid product was dried overnight by evaporation under air flow at room temperature to yield 1,3-dibromo-2-iodo-5-nitrobenzene (892.7 g, 82.9%). The product may optionally be purified further by recrystallization from ethanol.

Example 7

Preparation of 4-(2,6-dibromo-4-nitrophenoxy)-2-isopropylanisole

A 22 L jacketed vessel equipped with mechanical stirring and a nitrogen inlet adapter was charged with dimethylformamide (4 L) and 3-isopropyl-4-methoxyphenol (462.8 g, 2.59 moles). The solution was cooled to 0° C., and KHMDS (5.50 L of 0.5M toluene solution, 2.25 moles) was added over 1.5 h while maintaining the temperature of the mixture below 2° C. The reaction mixture was stirred for 30 min at 2° C., then 1,3-dibromo-2-iodo-5-nitro-benzene (798.6 g, 1.96 moles) was added in portions, still maintaining temperature of the mixture below 2° C. After the addition was complete, the reaction mixture was allowed to stir at room temperature for 2 h or until the reaction was complete as assayed by HPLC. The reaction mixture was cooled once more to 2° C. and ethyl acetate (4.5 L) was added, followed by slow addition of saturated aqueous sodium bicarbonate (6 L) while maintaining the temperature of the reaction mixture below 28° C. The organic layer was washed with saturated aqueous sodium chloride solution, then concentrated by rotary evaporation. The black, oily residue was taken up in acetone (3.87 L). Water (0.77 L) was added to the solution over 30 min with heating to 42° C. The solution was seeded with crystals of the product, cooled to 0° C., and stirred for 15 min. The resulting crystals of 4-(2,6-dibromo-4-nitrophenoxy)-2-isopropylanisole (665 g, 76.1%) were recovered by filtration and dried for 48 h by evaporation under air flow at room temperature.

Example 7A

Preparation of 4-(2,6-dibromo-4-nitrophenoxy)-2-isopropylanisole

3-Isopropyl-4-methoxyphenol (197.2 g, 1.19 moles) was dissolved in dimethylformamide (4 L). The mixture was stirred while the reaction vessel was cooled in an icewater bath. Sodium hydroxide (1.278 L of 11.0M aqueous solution, 1.278 moles) was added while maintaining the temperature of the reaction mixture below 35° C. 1,3-Dibromo-2-iodo-5-nitrobenzene (400.0 g, 0.983 moles) dissolved in dimethylformamide (portion of 4 L) was added to the reaction mixture over approximately 45 min. The reaction mixture was stirred at 20° to 25° C. for 24 h. Deionized water (2 L) was added over 2 h and the reaction mixture was cooled to 5° C. The resulting crystals of 4-(2,6-dibromo-4-nitrophenoxy)-2-isopropylanisole (405.4 g, 92.6%) were recovered by filtration and dried for 48 h by evaporation under air flow at room temperature.

Example 8

Preparation of 4-(2,6-dibromo-4-nitrophenoxy)-2-isopropylphenol

A 12 L three-necked round bottom flask equipped with a mechanical stirrer, an addition funnel, and a temperature probe was charged with 4-(2,6-dibromo-4-nitrophenoxy)-2-isopropylanisole (752.1 g, 1.69 moles), which was dissolved by stirring in dichloromethane (2 L) at room temperature. The mixture was cooled to 8.7° C. in an ice-water bath. A solution of boron tribromide (2.050 L, 1M in $CH_2Cl_2$, 2.05 moles) was added over 30 min. An increase of approximately 10° C. in the temperature of the reaction mixture was observed. The ice-water bath was removed and the reaction mixture was allowed to stir at room temperature until the reaction was complete, as assayed by HPLC. The reaction mixture was cooled once more in an ice-water bath, then quenched by slow addition of methanol (850 mL), during which the temperature of the reaction mixture was maintained below 18° C. Saturated aqueous sodium bicarbonate solution was added until the pH of the reaction mixture was 6 or 7. The aqueous phase was separated and washed with aliquots of ethyl acetate (2×1 L). The organic layers were combined and the solvent removed under a vacuum at room temperature to yield crude 4-(2,6-dibromo-4-nitrophenoxy)-2-isopropylphenol (796 g, 110%).

Example 9

Preparation of 4-(4-amino-2,6-dibromophenoxy)-2-isopropylphenol 4-(2,6-Dibromo-4-nitrophenoxy)-2-isopropylphenol (795 g, 1.84 moles) was divided into three roughly equal portions. Each portion was dissolved in THF (2.6 L) and charged into a 12 L three-necked round bottom flask equipped with a mechanical stirrer, addition funnel, and temperature probe. The solutions were heated to 33° C. Sodium dithionite (482 g, 2.4 moles) dissolved in deionized water (2.6 L) was added to each flask. The reaction temperature was held at 50° C. until each reaction was complete as assayed by HPLC. Hydrochloric acid (6N aqueous) was added dropwise to the heated reaction mixtures until their pH was about 3, and heating was continued for 45 min. The reaction mixtures were cooled to room temperature and their pH was adjusted to 6.6 by addition of saturated aqueous sodium bicarbonate solution. Ethyl acetate (2.5 L) was added to each flask with stirring for 2 min. Each reaction mixture was separated, and each organic layer was washed once with half-saturated aqueous sodium chloride solution, then once with saturated aqueous sodium chloride solution. The solvents were removed by rotary evaporation and the solids were dried overnight in a vacuum oven at 40° C. to yield crude 4-(4-amino-2,6-dibromophenoxy)-2-isopropylphenol (657 g, 96.9%). The crude 4-(4-amino-2,6-dibromophenoxy)-2-isopropylphenol was purified by recrystallization from isopropanol upon addition of 2.5 volumes of deionized water (90% recovery).

Example 10

Preparation of N-[3,5-dibromo-4-(4-hydroxy-3-isopropylphenoxy)phenyl]malonamic acid A slurry of 4-(4-amino-2,6-dibromophenoxy)-2-isopropylphenol (160 g, 0.401 mole) in t-butyl methyl ether (TBME, 1.07 L) was prepared in a 3 L, three-necked round bottom flask equipped with a mechanical stirrer, a thermocouple probe and an addition funnel. The mixture was cooled to 2° C. using a dry ice-acetone bath. A solution of sodium hydroxide (0.76M, 0.53 L, 0.401 mole) was added over 20 min while keeping the internal temperature of the reaction mixture below 2° C. Ethyl malonyl chloride (78.2 mL, 0.614 mole) was added via addition funnel to the biphasic mixture over 10 min while still maintaining the internal temperature below 2° C. The cooling bath was removed and the mixture was stirred for 40 min at room temperature. Fifteen minutes after the addition of malonyl chloride was completed, the reaction temperature was 5° C. and HPLC analysis of the reaction mixture failed to detect any remaining starting material. The reaction mixture was once more cooled to 2° C. using a dry ice-acetone bath, and a solution of sodium hydroxide (10.0 M, 176 mL, 1.76 moles) was added over 10 min. The internal temperature of the reaction mixture was maintained below 2° C. After the addition was complete, the cooling bath was removed and the mixture was stirred at room temperature. Two hours after the addition of NaOH was complete, the reaction temperature was 19° C. and none of the intermediate ethyl ester was detected by HPLC analysis. The organic layer was separated and extracted with water (150 mL). Any remaining traces of organic solvent were removed from the combined aqueous layers by distillation under reduced pressure. The aqueous solution was cooled in a dry ice-acetone bath to an internal temperature of 1° C. and acidified with HCl (10% aqueous, 1.25 L). The internal temperature of the mixture was maintained below 2° C. throughout the addition. The resultant precipitated solid was collected by filtration and washed twice with water. The solid was dried to constant weight in a vacuum oven at 40° C. to provide crude N-[3,5-dibromo-4-(4-hydroxy-3-isopropylphenoxy)phenyl]malonamic acid as a beige solid (219.5 g, 113%). The crude product was recrystallized with 90% recovery from methanol upon addition of water and cooling to 0° C.

Comparative Example

Acetic anhydride (9.9 g, 97.5 mmoles) was charged to a three-necked round bottom flask equipped with magnetic stirring, a nitrogen-inlet adapter, and an addition funnel. The acetic anhydride was cooled to a temperature of 20° to 25° C. by immersing the flask in a dry ice-ethanol bath. Fuming nitric acid (6 g, 94.9 mmoles) was added dropwise to the acetic anhydride while maintaining the internal temperature of the mixture. Iodine (1 g, 3.94 mmoles) was added in one portion, followed by the addition of trifluoroacetic anhydride (5.4 g, 47.3 mmoles). The reaction mixture, which contained the unisolated intermediate iodonium salt $(CF_3CO_2)_3$ I, was warmed to room temperature.

An aliquot of the reaction mixture (9 mL) in a Reactive System Screening Tool (RSST) was placed inside a bomb. The bomb was pressurized with nitrogen (300 psig at 15° C.) and heated at the rate of 1° C./min. The 10 mL glass cell of the RSST did not break; however, some of the reaction mixture erupted into the bomb, and the remainder of the aliquot changed color from red to dark purple-black.

Figure 1:
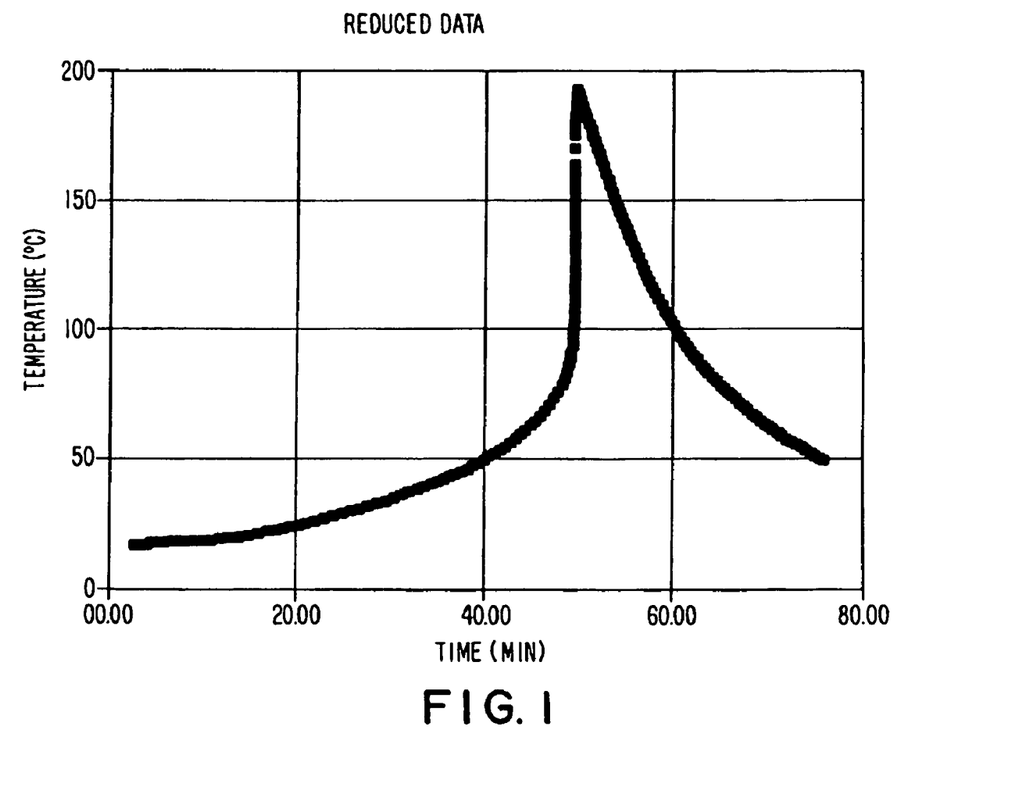
FIG. 1 is a graph of the results of a temperature vs. time study of the formation reaction of the iodonium triflate salt of the comparative example.

FIG. 1 is a graph of the resulting temperature vs. time measurements. It is apparent that an exothermic reaction began almost immediately with the commencement of heating. Similar results were obtained in differential scanning calorimetry (DSC) experiments. The data in FIG. 1, and the accompanying observations, illustrate that the thermal decomposition of the unisolated iodonium salt $(CF_3CO_2)_3I$ is so highly exothermic as to render $(CF_3CO_2)_3I$ hazardous as an intermediate in large scale preparations.

2-Isopropylphenol was reacted with methyl iodide in the presence of potassium carbonate to yield 1-isopropyl-2-methoxybenzene, which in turn was reacted with the solution of unisolated intermediate $(CF_3CO_2)_3I$ described above to form the bis-[3-isopropyl-4-methoxyphenyl]iodonium salt in 40-70% yield. The bis-[3-isopropyl-4-methoxyphenyl]iodonium salt precipitated as a gummy solid, making purification impracticable and contributing to the unpredictability of the yield.

The bis-[3-isopropyl-4-methoxyphenyl]iodonium salt was reacted with 2,6-dibromo-4-nitrophenol in the presence of elemental copper and triethylamine, over the course of 4 to 5 days in the dark, to form 4-(4-nitro-2,6-dibromophenoxy)-2-isopropylphenol in 50 to 80% yield. The extended time required for the ether formation, its unpredictable yield, and the unusual necessity to exclude light are inefficiencies that also militate against commercial practice of this synthetic route.

The entire disclosures of the patents and other publications cited above are incorporated herein by reference. While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A compound selected from the group consisting of compounds of formula A-II,

A-II wherein G represents a protecting group; M represents a metal; and R.sup.1 represents halogen, trifluoromethyl, an alkyl group of 1 to 6 carbons, or a cycloalkyl group of 3 to 7 carbons.

2. The compound according to claim 1, wherein said compound is hydroxy-(3-isopropyl-4-methoxyphenyl)methanesulfonic acid, sodium salt.

* * * * *